(12) United States Patent
Dai et al.

(10) Patent No.: US 10,246,630 B2
(45) Date of Patent: Apr. 2, 2019

(54) WATER SOLUTION, CLEAN FRACTURING FLUID AND METHOD FOR FRACTURING RESERVOIR

(71) Applicants: China University of Petroleum(East China), Qingdao, Shandong (CN); Research Institute of Petroleum Exploration & Development, Haidian District, Beijing (CN)

(72) Inventors: Caili Dai, Qingdao (CN); Mingwei Zhao, Qingdao (CN); He Liu, Beijing (CN); Yining Wu, Qingdao (CN); Guang Zhao, Qingdao (CN); Yongpeng Sun, Qingdao (CN); Xuepeng Wu, Qingdao (CN)

(73) Assignee: CHINA UNIVERSITY OF PETROLEUM (EAST CHINA) (CN)

( * ) Notice: Subject to any disclaimer, the term of this patent is extended or adjusted under 35 U.S.C. 154(b) by 0 days.

(21) Appl. No.: 15/668,273

(22) Filed: Aug. 3, 2017

(65) Prior Publication Data
US 2018/0334611 A1    Nov. 22, 2018

(30) Foreign Application Priority Data

May 19, 2017    (CN) .......................... 2017 1 0359670

(51) Int. Cl.
*C09K 8/68*    (2006.01)
*C07C 233/05*    (2006.01)
(Continued)

(52) U.S. Cl.
CPC ................ *C09K 8/68* (2013.01); *C07C 57/13* (2013.01); *C07C 57/145* (2013.01); *C07C 57/46* (2013.01); *C07C 233/05* (2013.01); *C07C 309/04* (2013.01); *C09K 8/72* (2013.01); *C09K 2208/26* (2013.01)

(58) Field of Classification Search
None
See application file for complete search history.

(56) References Cited

U.S. PATENT DOCUMENTS

2002/0147114 A1* 10/2002 Dobson, Sr. ............. C09K 3/00
  507/242
2004/0214725 A1* 10/2004 Moss .................. B01F 17/0042
  507/129

(Continued)

*Primary Examiner* — John J Figueroa
(74) *Attorney, Agent, or Firm* — Calfee, Halter & Griswold LLP

(57) ABSTRACT

The present invention relates to the fracturing field, and discloses a water solution, a clean fracturing fluid, and a method for fracturing reservoir. The water solution contains organic acid amidopropyl dimethylamine, an additive, and water, wherein, the additive is at least one of salicylate, cis-butenedioic acid, o-phthalic acid, dodecyl sulfonate, p-toluene sulfonate, and benzoate. The water solution has high carbon dioxide response performance, a clean fracturing fluid that contains the water solution has superior cyclic utilization performance, and the fracturing fluid can solve the problems of conventional fracturing fluids used in fracturing stimulation of oil and gas reservoirs, including incomplete gel breaking, severe damages to the reservoir, and severe contamination of flow-back fluid, etc.

14 Claims, 3 Drawing Sheets

(51) Int. Cl.
*C07C 57/145* (2006.01)
*C07C 57/13* (2006.01)
*C07C 57/46* (2006.01)
*C07C 309/04* (2006.01)
*C09K 8/72* (2006.01)

(56) References Cited

U.S. PATENT DOCUMENTS

2006/0025321 A1* 2/2006 Treybig .................. C09K 8/68
 510/382
2008/0248977 A1* 10/2008 Knox ....................... A61K 8/02
 507/240

* cited by examiner

WATER SOLUTION, CLEAN FRACTURING FLUID AND METHOD FOR FRACTURING RESERVOIR

CROSS REFERENCE TO RELATED APPLICATIONS

This application claims priority to Chinese Application No. 201710359670.6, filed on May 19, 2017, entitled "A Recyclable and $CO_2$-Response Clean Fracturing Fluid", which is specifically and entirely incorporated by reference.

FIELD OF THE INVENTION

The present invention relates to the fracturing field, in particular to a water solution, a clean fracturing fluid prepared from the water solution, and a method for fracturing a reservoir with the clean fracturing fluid.

BACKGROUND OF THE INVENTION

As the oil and gas industry is developed, unconventional gas reservoirs (tight sandstone gas, coal-bed gas, and shale gas) have become a new developing trend of the global low-carbon economy, and their exploration and development has been scaled up gradually. Among proved oil reserves in China, low-permeability oilfields account for one quarter or higher share. As most oil fields enter into a high water-cut stage, the exploitation becomes more and more difficult. Exploiting those oil and gas fields is of far-reaching importance for maintaining stability of the oil energy resources in China.

Fracturing techniques have been widely applied as conventional stimulation and stimulated injection techniques for oil and gas fields. Fracturing fluids are one of the keys in fracturing operation, and are often referred to as fracturing "blood". Fracturing fluids that are applied the most widely at present are slickwater fracturing fluids and guanidine gel fracturing fluids. However, slickwater fracturing fluids have low viscosity and limited solid carrying capacity; guanidine gel fracturing fluids may cause severe damages to the reservoirs. Clean fracturing fluids have outstanding performance in actual oil and gas mining, and have received extensive attention from domestic and foreign researchers and have been applied gradually owing to a series of advantages, including simple molecular structure, high dissolvability, fewer damages to reservoirs, and good viscosity breaking performance, etc. However, for unconventional oil and gas reservoirs, the demand for fracturing fluid and water resource is high owing to great well depth and long horizontal section, and the flow-back fluid generated after fracturing not only involves high treatment cost, but also may result in severe environmental pollution if it is discharged to the external environment. Moreover, owing to the fact that the molecular structure of slickwater fracturing fluid or guanidine gel fracturing fluid is changed or destroyed after gel breaking, complex chemical and physical treatment is required or a large quantity of original fluid has to be added to the flow-back fluid, before the flow-back fluid can be reused. Therefore, how to efficiently utilize the large quantity of flow-back fluid is a challenge in efficient fracturing stimulation of unconventional oil and gas reservoirs at present. Reuse of flow-back fluid is a future developing trend of the oil and gas field industry, in consideration of the cost and environmental protection aspects.

SUMMARY OF THE INVENTION

To overcome the above-mentioned defects in the fracturing fluids in the prior art, the present invention provides a water solution, a clean fracturing fluid, and a method for fracturing reservoir. The water solution provided in the present invention can be introduced with carbon dioxide for gelatinization, and then introduced with air, nitrogen, or an inert gas for gel breaking, so as to realize cyclic utilization of a fracturing fluid, and solve the problems in conventional fracturing fluids used in fracturing stimulation of oil and gas reservoirs, including incomplete gel breaking, severe damages to the reservoir, and severe contamination of the flow-back fluid, etc.

In a first aspect, the present invention provides a water solution, which contains organic acid amidopropyl dimethylamine, an additive, and water, wherein, the additive is at least one of salicylate, cis-butenedioic acid, o-phthalic acid, dodecyl sulfonate, p-toluene sulfonate, and benzoate.

In a second aspect, the present invention provides a clean fracturing fluid, which is a mixture obtained by introducing carbon dioxide into a water solution for gelatinization, wherein, the water solution contains organic acid amidopropyl dimethylamine, an additive, and water, wherein, the additive is selected from at least one of salicylate, cis-butenedioic acid, o-phthalic acid, dodecyl sulfonate, p-toluene sulfonate, and benzoate.

In a third aspect, the present invention provides a method for fracturing reservoir, which comprises: injecting the clean fracturing fluid provided in the present invention into a reservoir for fracturing, and introducing air, nitrogen, or an inert gas into the reservoir after the fracturing for gel breaking.

The present invention attains the following beneficial effects:

(1.) The water solution described in the present invention can be gelatinized easily, the clean fracturing fluid obtained after gelatinization can be treated with a simple method for complete gel breaking, and the flow-back is easy, so that the water solution can be utilized cyclically easily.

(2.) All of the reagents used in the gelatinization process of the water solution and the gel breaking process of the clean fracturing fluid in the present invention are non-toxic and harmless gasses, which are convenient to use, cheap, and widely available.

(3.) The present invention not only overcomes the drawbacks of the conventional fracturing fluids, including incomplete gel breaking and severe damages to the reservoir, etc., but also solves the problems of high cost of clean fracturing fluid and severe contamination of the flow-back fluid, etc.;

(4.) The present invention can save cost and realize resource exploitation and environmental protection.

DETAILED DESCRIPTION

Figure 1:
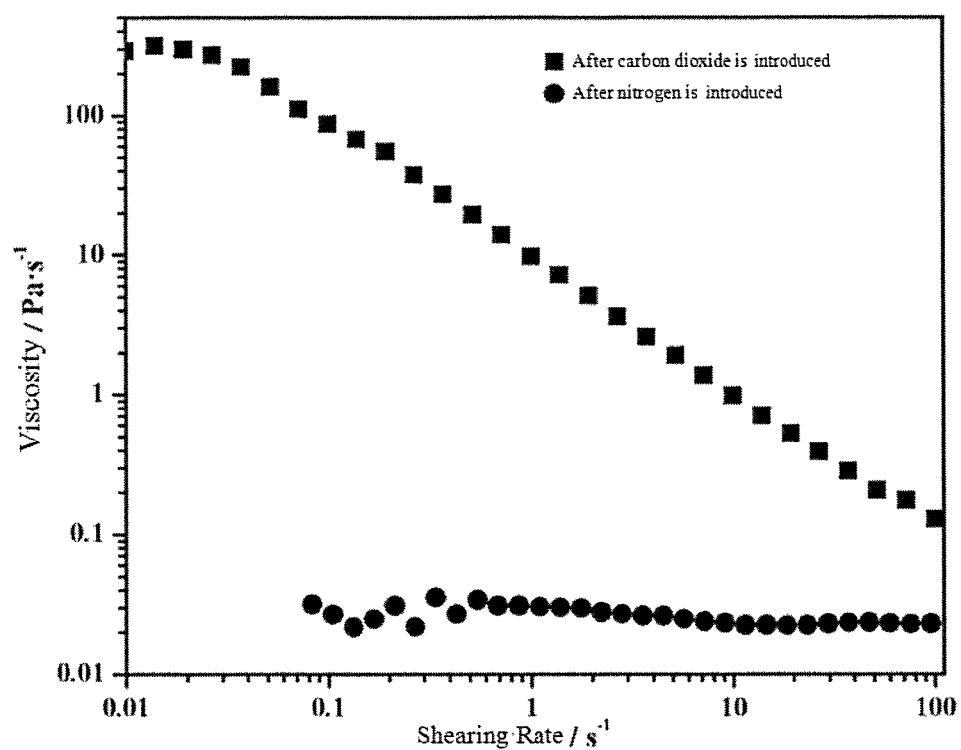
FIG. 1 is a diagram of shear viscosity of the clean fracturing fluid in example 1 vs. shearing rate.

The ends points and any value in the ranges disclosed in the present invention are not limited to the exact ranges or values; instead, those ranges or values shall be comprehended as encompassing values that are close to those ranges or values. For numeric ranges, the end points of the ranges, the end points of the ranges and the discrete point values, and the discrete point values may be combined to obtain one or more new numeric ranges, which shall be deemed as having been disclosed specifically in this document.

In a first aspect, the present invention provides a water solution, which contains organic acid amidopropyl dimethylamine, an additive, and water, wherein, the additive is at least one of salicylate, cis-butenedioic acid, o-phthalic acid, dodecyl sulfonate, p-toluene sulfonate, and benzoate, preferably is at least one of salicylate, cis-butenedioic acid, and p-toluene sulfonate.

In the present invention, preferably, the organic acid amidopropyl dimethylamine is at least one of palmitamidopropyl dimethylamine, stearamidopropyl dimethylamine, oleamidopropyl dimethylamine, erucamidopropyl dimethylamine, and behenamidopropyl dimethylamine. Further preferably, the organic acid amidopropyl dimethylamine is at least one of stearamidopropyl dimethylamine, oleamidopropyl dimethylamine, and erucamidopropyl dimethylamine. In the further preferred embodiment, the cyclic gelatinizing and gel breaking performance of the water solution is better.

In the present invention, though the contents of the components in the water solution may vary within wide ranges, to improve the cyclic gelatinizing and gel breaking performance of the water solution, preferably, based on the total weight of the water solution, the content of the organic acid amidopropyl dimethylamine is 1-6 wt % (e.g., 1 wt %, 1.5 wt %, 2 wt %, 2.5 wt %, 3 wt %, 3.5 wt %, 4 wt %, 4.5 wt %, 5 wt %, 5.5 wt %, 6 wt %, or 6.5 wt %), the content of the additive is 0.1-0.6 wt % (e.g., 0.15 wt %, 0.2 wt %, 0.25 wt %, 0.3 wt %, 0.35 wt %, 0.4 wt %, 0.45 wt %, 0.5 wt %, 0.55 wt %, or 0.6 wt %), and the content of water is 93.4-98.9 wt % (e.g., 94 wt %, 94.5 wt %, 95 wt %, 95.5 wt %, 96 wt %, 96.5 wt %, 97 wt %, 97.5 wt %, 98 wt %, or 98.5 wt %).

In the present invention, to further improve the cyclic gelatinizing and gel breaking performance of the water solution, preferably, the organic acid amidopropyl dimethylamine and the additive have a weight ratio of 8-12:1 (e.g., 8:1, 8.5:1, 8.5:1, 9:1, 9.5:1, 10:1, 10.5:1, 11:1, 11.5:1, or 12:1), preferably 9.5-10.5:1, more preferably 10:1.

The method for preparing the water solution in the present invention may be: mixing the organic acid amidopropyl dimethylamine, the additive, and the water.

In the present invention, to prevent agglomeration or inhomogeneous mixing of the components, preferably, the mixing process is executed while stirring. The mixing conditions preferably include: temperature of 30-50° C., time of 5-20 min.

In the present invention, the mixed solution is kept still to obtain a water solution that has certain viscosity.

In a second aspect, the present invention provides a clean fracturing fluid, which is a mixture obtained by introducing carbon dioxide into a water solution for gelatinization, wherein, the water solution is the above water solution provided in the present invention.

In the present invention, the water solution is in a turbid state; after carbon dioxide is introduced into the water solution, the water solution is turned into a clean fracturing fluid with high viscoelasticity, which is in a clear state. To improve the performance of the clean fracturing fluid, preferably, the carbon dioxide is introduced at a rate of 0.1-0.5 L/min., the amount of carbon dioxide is used such that the system is clear.

In the process of introducing carbon dioxide into the water solution, the carbon dioxide introducing time may be determined according to the required quantity of carbon dioxide; for example, the carbon dioxide introducing time may be 1-2 min.

In a third aspect, the present invention provides a method for fracturing reservoir, which comprises: injecting the above clean fracturing fluid provided in the present invention into a reservoir for fracturing, and introducing air, nitrogen, or an inert gas into the reservoir after the fracturing for gel breaking.

In the present invention, the inert gas may be argon, helium or neon, preferably is argon.

In the present invention, the flow-back fluid obtained after gel breaking of the clean fracturing fluid may be introduced with carbon dioxide again for gelatinization, and then is used as the clean fracturing fluid again, so that the clean fracturing fluid is utilized cyclically.

In the present invention, the content of the organic acid amidopropyl dimethylamine in the water solution may vary, depending on the reservoir temperature; preferably, when the reservoir temperature is lower than 50° C., the water solution contain 1-2 wt % organic acid amidopropyl dimethylamine; when the reservoir temperature is 50-80° C., the water solution contains 2-4 wt % organic acid amidopropyl dimethylamine; when the reservoir temperature is 80-95° C., the water solution contains 4-6 wt % organic acid amidopropyl dimethylamine. In the above preferred embodiment, a better reservoir fracturing effect can be attained.

Hereunder the present invention will be detailed in embodiments. In the following embodiments:

The stearamidopropyl dimethylamine is prepared with the following method:

Stearic acid and N,N-dimethylaminopropylamine are loaded at the molar ratio of 1:1.2 into a three-neck flask with a condenser tube and a reflux divider, sodium fluoride is added as a catalyst, calcium chloride is added as a dehydrator into the reflux divider, and condensation reaction is executed under nitrogen shielding at 120-150° C. for 8 h; unreacted N,N-dimethylaminopropylamine is removed by rotary evaporation after the reaction stops, a mixed solvent of acetone and water is added into the crude product to remove sodium fluoride and unreacted raw materials and impurities, and then the crude product is filtered and washed with a mixed solvent of acetone and water (acetone and water have a volume ratio of 2:1); thus, the target product—stearamidopropyl dimethylamine in a white solid form is obtained;

The erucamidopropyl dimethylamine is purchased from Shanghai Winsono New Material Technology Co., Ltd., with designation as Winsono PKOE;

The oleamidopropyl dimethylamine is purchased from Shanghai Winsono New Material Technology Co., Ltd., with designation as Winsono PKO 1898;

The behenamidopropyl dimethylamine is purchased from Shanghai Winsono New Material Technology Co., Ltd., with designation as Winsono PKOB;

The palmitamidopropyl dimethylamine is prepared with the following method:

Palmic acid and N,N-dimethylaminopropylamine are loaded at the molar ratio of 1:1.2 into a three-neck flask with a condenser tube and a reflux divider, sodium fluoride is added as a catalyst, calcium chloride is added as a dehydrator into the reflux divider, and condensation reaction is executed under nitrogen shielding at 120-150° C. for 8 h; unreacted N,N-dimethylaminopropylamine is removed by rotary evaporation after the reaction stops, a mixed solvent of acetone and water is added into the crude product to remove sodium fluoride and unreacted raw materials and impurities, and then the crude product is filtered and washed with a mixed solvent of acetone and water (acetone and water have a volume ratio of 2:1); thus, the target product—white powder palmitamidopropyl dimethylamine is obtained;

The sodium p-toluenesulfonate is purchased from Shanghai Aladdin Biochemical Technology Co., Ltd., with designation as T108370;

The cis-butenedioic acid is purchased from Shanghai Aladdin Biochemical Technology Co., Ltd., with designation as M108865;

The sodium salicylate is purchased from Shanghai Aladdin Biochemical Technology Co., Ltd., with designation as S104177;

The o-phthalic acid is purchased from Shanghai Aladdin Biochemical Technology Co., Ltd., with designation as P104114;

The sodium dodecyl sulfate is purchased from Shanghai Aladdin Biochemical Technology Co., Ltd., with designation as S105389;

The sodium benzoate is purchased from Shanghai Aladdin Biochemical Technology Co., Ltd., with designation as S104124;

The rheometer is purchased from ThermoFisher Scientific, with designation as HAAKE MARS 60 Rheometer.

Example 1

3 g stearamidopropyl dimethylamine in a white solid form and 0.3 g sodium p-toluenesulfonate are loaded into a beaker filled with 96.7 g water while stirring, the mixture is stirred further for 10 min. at 40° C., and then is kept still, to obtain a water solution (the viscosity of the system is 18 mPa·s), carbon dioxide is introduced into the obtained water solution for 1-2 min. (at a rate of 0.2 L/min.), and then the water solution is sealed and kept still; thus, a clean fracturing fluid A1 (containing 3 wt % stearamidopropyl dimethylamine, 0.3 wt % sodium p-toluenesulfonate, and water (accounting for the remaining content)) is obtained.

Example 2

5 g erucamidopropyl dimethylamine in a white block form and 0.5 g cis-butenedioic acid are loaded into a beaker filled with 94.5 g water while stirring, the mixture is stirred further for 10 min. at 40° C., and then is kept still, to obtain a water solution (the viscosity of the system is 19 mPa·s), carbon dioxide is introduced into the obtained water solution for 1-2 min. (at a rate of 0.2 L/min.), and then the water solution is sealed and kept still; thus, a clean fracturing fluid A2 (containing 5 wt % erucamidopropyl dimethylamine, 0.5 wt % cis-butenedioic acid, and water (accounting for the remaining content)) is obtained.

Example 3

2 g oleamidopropyl dimethylamine in a yellow oil form and 0.2 g sodium salicylate are loaded into a beaker filled with 97.8 g water while stirring, the mixture is stirred further for 10 min. at 40° C., and then is kept still, to obtain a cream-colored water solution (the viscosity of the system is 9 mPa·s), carbon dioxide is introduced into the obtained water solution for 1-2 min. (at a rate of 0.2 L/min.), and then the water solution is sealed and kept still; thus, a clean fracturing fluid A2 (containing 2 wt % oleamidopropyl dimethylamine, 0.2 wt % sodium salicylate, and water (accounting for the remaining content)) is obtained.

Example 4

A clean fracturing fluid is prepared with the method described in the example 2, but the amount of erucamidopropyl dimethylamine is 9 g, the amount of cis-butenedioic acid is 0.9 g, and the amount of water is 90.1 g. Thus, a clean fracturing fluid A4 (containing 9 wt % erucamidopropyl dimethylamine, 0.9 wt % cis-butenedioic acid, and water (accounting for the remaining content)) is obtained.

Example 5

A clean fracturing fluid is prepared with the method described in the example 2, but the amount of cis-butenedioic acid is 0.3 g. Thus, a clean fracturing fluid A5 (containing 5 wt % erucamidopropyl dimethylamine, 0.3 wt % cis-butenedioic acid, and water (accounting for the remaining content)) is obtained.

Example 6

A clean fracturing fluid is prepared with the method described in the example 2, but the erucamidopropyl dimethylamine is replaced with palmitamidopropyl dimethylamine in the same weight. Thus, a clean fracturing fluid A6 (containing 5 wt % palmitamidopropyl dimethylamine, 0.5 wt % cis-butenedioic acid, and water (accounting for the remaining content)) is obtained.

Example 7

A clean fracturing fluid is prepared with the method described in the example 2, but the erucamidopropyl dimethylamine is replaced with behenamidopropyl dimethylamine in the same weight. Thus, a clean fracturing fluid A6 (containing 5 wt % behenamidopropyl dimethylamine, 0.5 wt % cis-butenedioic acid, and water (accounting for the remaining content)) is obtained.

Example 8

A clean fracturing fluid is prepared with the method described in the example 2, but the cis-butenedioic acid is replaced with o-phthalic acid in the same weight. Thus, a clean fracturing fluid A7 (containing 5 wt % erucamidopropyl dimethylamine, 0.5 wt % o-phthalic acid, and water (accounting for the remaining content)) is obtained.

Example 9

A clean fracturing fluid is prepared with the method described in the example 2, but the cis-butenedioic acid is replaced with sodium dodecyl sulfate in the same weight. Thus, a clean fracturing fluid A7 (containing 5 wt % erucamidopropyl dimethylamine, 0.5 wt % dodecyl sulfonate, and water (accounting for the remaining content)) is obtained.

Example 10

A clean fracturing fluid is prepared with the method described in the example 2, but the cis-butenedioic acid is replaced with sodium benzoate in the same weight. Thus, a clean fracturing fluid A7 (containing 5 wt % erucamidopropyl dimethylamine, 0.5 wt % sodium benzoate, and water (accounting for the remaining content)) is obtained.

Example 11

A clean fracturing fluid is prepared with the method described in the example 2, but carbon dioxide is introduced at a rate of 1 L/min. till the system is clear. Thus, a clean fracturing fluid A8 is obtained.

Test Cases

Initial zero shear viscosity and viscoelasticity at room temperature (25° C.) and normal pressure (101.3 kPa)

Figure 3:
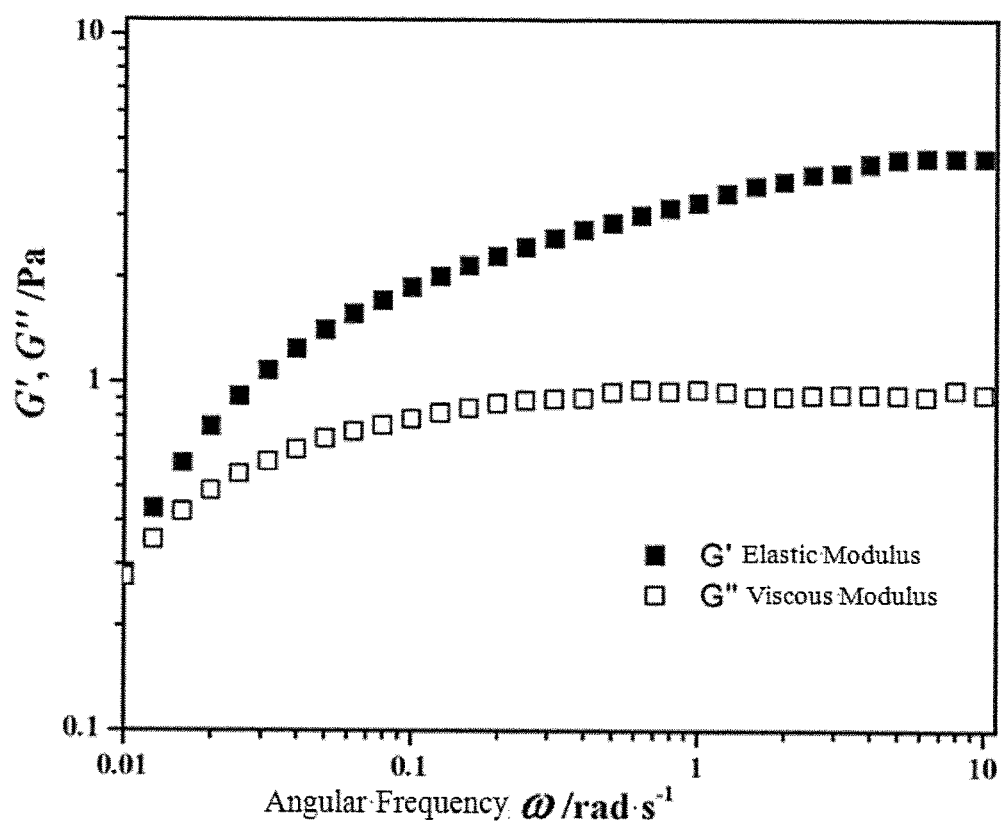
FIG. 3 is a diagram of viscoelastic modulus of the clean fracturing fluid in the example 1 vs. oscillation frequency.

100 mL sample of the clean fracturing fluid A1 is taken, the variation of shear viscosity with shearing rate (0.1-100 s$^{-1}$) and the variation of viscoelastic modulus with angular frequency (0.01-10 rad·s$^{-1}$) of the sample A1 are tested with an open coaxial cylinder module in the rheometer; the results are shown in FIGS. 1 and 3. The zero shear viscosity of the system is extrapolated from the relation curve of shear viscosity vs. shearing rate, and is referred to as initial zero shear viscosity; the result is shown in Table 1; the viscoelasticity of the system is judged from the diagram of viscoelastic modulus vs. angular frequency.

100 mL samples of the clean fracturing fluid A2-A11 are taken respectively, and the variation of shear viscosity with shearing rate (0.1-100 s$^{-1}$) of each of the samples A2-A11 is tested with the open coaxial cylinder module in the rheometer respectively; the zero shear viscosity of each of the samples A2-A11 is extrapolated from the relation curve of shear viscosity vs. shearing rate, and is referred to as initial zero shear viscosity; the results are shown in Table 1.

Shear Viscosity at High Temperature and High Pressure (3 MPa)

100 mL sample of the clean fracturing fluid A1 is taken, the shear viscosity of the sample A1 after shearing for 2 h at 70° C., 170 s$^{-1}$ shearing rate, and 3 MPa $CO_2$ pressure is measured respectively, and is referred to as HTHP viscosity; the result is shown in Table 1;

100 mL samples of the clean fracturing fluids A2 and A4-A11 are taken respectively, the shear viscosity of each of the sample A2 and A4-A11 after shearing for 2 h at 85° C., 170 s$^{-1}$ shearing rate, and 3 MPa $CO_2$ pressure is measured respectively, and is referred to as HTHP viscosity; the results are shown in Table 1;

100 mL sample of the clean fracturing fluid A3 is taken, the shear viscosity of the sample A3 after shearing for 2 h at 45° C., 170 s$^{-1}$ shearing rate, and 3 MPa $CO_2$ pressure is measured, and is referred to as HTHP viscosity; the result is shown in Table 1.

Test of Cyclic Performance of Clean Fracturing Fluid 50 mL samples of the clean fracturing fluids A1-A11 are taken respectively, nitrogen is introduced into each of the samples for 15 min. for gel breaking respectively, so that the system is turned into a turbid fluid with lower viscosity, the viscosity of the system after gel breaking is measured with a rheometer, and then carbon dioxide is introduced (first carbon dioxide introduced cycle), so that the system is turned into a clear high-viscosity fluid within 2 min., the zero shear viscosity of the system is measured with a rheometer. The operations are repeated for three times. The viscosity of the sample A1 after the first nitrogen introduced cycle is shown in FIG. 1, the cyclic performance test result of the sample A1 is shown in FIG. 2 and Table 1, and the test results of the samples A2-A11 are shown in Table 1.

Figure 2:
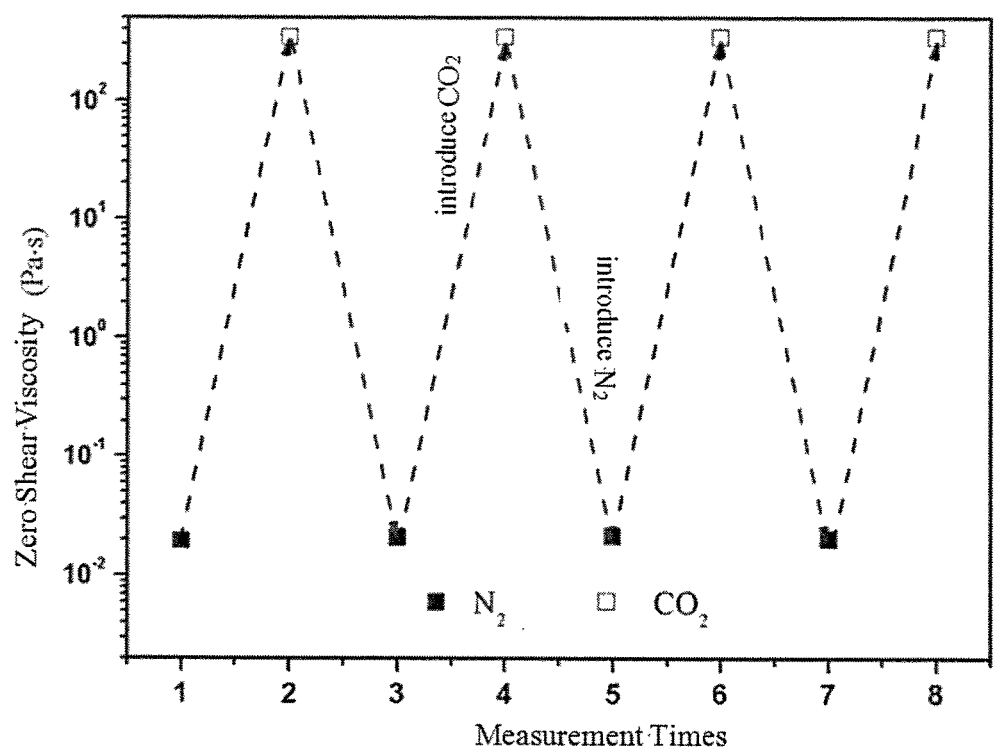
FIG. 2 shows the viscosity change of the system after carbon dioxide and nitrogen are introduced repeatedly into the clean fracturing fluid in the example 1.

It is seen from FIG. 1: the water solution in the present invention has good $CO_2$ response performance; it is seen from FIG. 2: the clean fracturing fluid in the present invention has superior cyclic utilization performance; it is seen from FIG. 3: within the range of angular frequency used in the test, the elastic modulus of the sample A1 is always greater than the viscous modulus, which indicates that the clean fracturing fluid in the present invention has good viscoelasticity, and can carry solids by means of its elasticity, i.e., the clean fracturing fluid has good solid carrying performance.

TABLE 1

| | Initial zero shear viscosity/ Pa · s | HTHP viscosity/ mPa · s | Viscosity after the first gel breaking cycle/ mPa · s | Viscosity after the first $CO_2$ introduced cycle/Pa · s | Viscosity after the third gel breaking cycle/ mPa · s | Viscosity after the third $CO_2$ introduced cycle/Pa · s |
|---|---|---|---|---|---|---|
| A1 | 300 | 55 | 20 | 293 | 18 | 291 |
| A2 | 1800 | 50 | 14 | 1800 | 20 | 1780 |
| A3 | 10 | 45 | 11 | 9.8 | 16 | 9.6 |
| A4 | 3230 | 200 | 46 | 3225 | 50 | 3220 |
| A5 | 2785 | 178 | 35 | 2763 | 35 | 2759 |
| A6 | 562 | 68 | 36 | 560 | 35 | 530 |
| A7 | 2210 | 211 | 67 | 2220 | 62 | 2150 |
| A8 | 23 | 30 | 12 | 22 | 12 | 20 |
| A9 | 543 | 35 | 22 | 549 | 21 | 515 |
| A10 | 886 | 42 | 16 | 890 | 15 | 887 |
| A11 | 1795 | 50 | 20 | 1800 | 22 | 1745 |

It is seen from Table 1: the clean fracturing fluid in the present invention has high initial zero shear viscosity and high temperature-resistant and pressure-resistant performance; thus, it is seen that the water solution in the present invention has good $CO_2$ response performance; in addition, when $CO_2$ is introduced after 3 gel breaking cycles, the system still have viscosity comparable to the initial zero shear viscosity, which indicates that the clean fracturing fluid in the present invention has superior cyclic utilization performance. The viscosity of a system will decrease as the temperature increases. According to the viscosity characteristics of different systems at different temperatures, it is seen from Table 1: the clean fracturing fluid A1 is more suitable for reservoirs at moderate temperature (50-80° C.), the clean fracturing fluid A2 is more suitable for reservoirs at high temperature (80-95° C.), and the clean fracturing fluid A3 is more suitable for reservoirs at low temperature (lower than 50° C.).

While the present invention is described above in detail in some preferred embodiments, the present invention is not limited to those embodiments. Various simple variations, including combinations of the technical features in any other appropriate way, can be made to the technical scheme of the present invention within the scope of the technical concept of the present invention, but such variations and combinations shall be deemed as disclosed content in the present invention and falling in the protection scope of the present invention.

The invention claimed is:

1. A method for fracturing a reservoir, comprising:
preparing an aqueous solution by:
mixing an organic acid amidopropyl dimethylamine, an additive, and water, while stirring at a temperature of 30° C. to 50° C. for a time of 5 min to 20 min,
wherein the additive is selected from the group consisting of salicylate, cis-butenedioic acid, o-phthalic acid, dodecyl sulfonate, p-toluene sulfonate, benzoate and combinations thereof,
wherein a weight ratio of the organic acid amidopropyl dimethylamine and the additive is 8:1-12:1;
introducing carbon dioxide at a rate of 0.1-0.5 L/min. into the aqueous solution for gelatinization, to form a clean fracturing fluid,
wherein the carbon dioxide is introduced for a time sufficient render the clean fracturing fluid clear;
injecting the clean fracturing fluid into a reservoir for fracturing; and
introducing air, nitrogen, or an inert gas into the reservoir after the fracturing for gel breaking.

2. The method for fracturing a reservoir of claim 1, wherein the organic acid amidopropyl dimethylamine is selected from the group consisting of palmitamidopropyl dimethylamine, stearamidopropyl dimethylamine, oleamidopropyl dimethylamine, erucamidopropyl dimethylamine, behenamidopropyl dimethylamine, and combinations thereof.

3. The method for fracturing a reservoir of claim 1, wherein, based on the total weight of the aqueous solution, the amount of the organic acid amidopropyl dimethylamine is 1-6 wt %, the amount of the additive is 0.1-0.6 wt %, and the amount of water is 93.4-98.9 wt %.

4. The method for fracturing a reservoir of claim 1, wherein a weight ratio of the organic acid amidopropyl dimethylamine and the additive is 9.5:1-10.5:1.

5. The method for fracturing a reservoir of claim 1, wherein, when the reservoir temperature is lower than 50° C., the aqueous solution contains 1-2 wt % organic acid amidopropyl dimethylamine; when the reservoir temperature is 50-80° C., the aqueous solution contains 2-4 wt % organic acid amidopropyl dimethylamine; when the reservoir temperature is 80-95° C., the aqueous solution contains 4-6 wt % organic acid amidopropyl dimethylamine.

6. The method of claim 1, wherein the additive is selected from the group consisting of salicylate, cis-butenedioic acid, dodecyl sulfonate, p-toluene sulfonate, benzoate, and combinations thereof.

7. A method of preparing an aqueous solution for use in fracturing a reservoir, the method comprising:
mixing an organic acid amidopropyl dimethylamine, an additive, and water, while stirring at a temperature of 30° C. to 50° C. for a time of 5 min to 20 min;
wherein, the additive is selected from the group consisting of salicylate, cis-butenedioic acid, o-phthalic acid, dodecyl sulfonate, p-toluene sulfonate, benzoate and combinations thereof;
wherein a weight ratio of the organic acid amidopropyl dimethylamine and the additive is 8:1-12:1.

8. The method of claim 7, wherein the organic acid amidopropyl dimethylamine is selected from the group consisting of palmitamidopropyl dimethylamine, stearamidopropyl dimethylamine, oleamidopropyl dimethylamine, erucamidopropyl dimethylamine, behenamidopropyl dimethylamine, and combinations thereof.

9. The method of claim 7, wherein, based on the total weight of the aqueous solution, the content of the organic acid amidopropyl dimethylamine is 1-6 wt %, the content of the additive is 0.1-0.6 wt %, and the content of water is 93.4-98.9 wt %.

10. The aqueous solution of claim 7, wherein a weight ratio of the organic acid amidopropyl dimethylamine and the additive is 9.5:1-10.5:1.

11. A method of preparing a clean fracturing fluid, comprising:
preparing an aqueous solution by:
mixing an organic acid amidopropyl dimethylamine, an additive, and water, while stirring at a temperature of 30° C. to 50° C. for a time of 5 min to 20 min,
wherein the additive is selected from the group consisting of salicylate, cis-butenedioic acid, o-phthalic acid, dodecyl sulfonate, p-toluene sulfonate, benzoate and combinations thereof,
wherein a weight ratio of the organic acid amidopropyl dimethylamine and the additive is 8:1-12:1;
introducing carbon dioxide at a rate of 0.1-0.5 L/min. into the aqueous solution for gelatinization, wherein the carbon dioxide is introduced for a time sufficient render the clean fracturing fluid clear.

12. The method of claim 11, wherein the organic acid amidopropyl dimethylamine is selected from the group consisting of palmitamidopropyl dimethylamine, stearamidopropyl dimethylamine, oleamidopropyl dimethylamine, erucamidopropyl dimethylamine, behenamidopropyl dimethylamine, and combinations thereof.

13. The method of claim 11, wherein, based on the total weight of the aqueous solution, the content of the organic acid amidopropyl dimethylamine is 1-6 wt %, the content of the additive is 0.1-0.6 wt %, and the content of water is 93.4-98.9 wt %.

14. The method of claim 11, wherein a weight ratio of the organic acid amidopropyl dimethylamine and the additive is 9.5:1-10.5:1.

* * * * *